(12) United States Patent
Konishi et al.

(10) Patent No.: US 8,226,646 B2
(45) Date of Patent: Jul. 24, 2012

(54) HIGH FREQUENCY TREATMENT INSTRUMENT

(75) Inventors: Sumihito Konishi, Akishima (JP); Kazunori Taniguchi, Hachioji (JP); Kazuya Hijii, Tama (JP); Yoshitaka Honda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1194 days.

(21) Appl. No.: 11/501,641

(22) Filed: Aug. 9, 2006

(65) Prior Publication Data

US 2007/0049921 A1 Mar. 1, 2007

(30) Foreign Application Priority Data

Aug. 10, 2005 (JP) .................................. 2005-232139

(51) Int. Cl.
*A61B 18/14* (2006.01)
(52) U.S. Cl. ................ 606/45; 606/46; 606/49
(58) Field of Classification Search .................... 606/45, 606/46, 49
See application file for complete search history.

(56) References Cited

U.S. PATENT DOCUMENTS

| | | | | |
|---|---|---|---|---|
| 1,814,791 A | * | 7/1931 | Ende ................................ | 606/50 |
| 3,920,021 A | * | 11/1975 | Hiltebrandt ...................... | 606/50 |
| 3,987,795 A | * | 10/1976 | Morrison ......................... | 606/48 |
| 5,078,716 A | * | 1/1992 | Doll ................................. | 606/47 |
| 5,925,045 A | * | 7/1999 | Reimels et al. .................. | 606/48 |
| 6,942,662 B2 | * | 9/2005 | Goble et al. ..................... | 606/48 |
| 7,371,236 B2 | * | 5/2008 | Okada ............................. | 606/45 |
| 7,618,416 B2 | * | 11/2009 | Ono et al. ........................ | 606/45 |
| 7,632,266 B2 | * | 12/2009 | Scopton et al. .................. | 606/41 |
| 7,744,591 B2 | * | 6/2010 | Rioux et al. ..................... | 606/32 |

FOREIGN PATENT DOCUMENTS

| | | |
|---|---|---|
| JP | 54-087696 | 6/1979 |
| JP | 06-292685 | 10/1994 |
| JP | 08-299355 | 11/1996 |
| JP | 2003-290248 | 10/2003 |

OTHER PUBLICATIONS

Official Action, mailed Feb. 15, 2011, from the Japan Patent Office in counterpart Japanese Patent Application No. 2005-232139, together with a partial English translation.
Official Action, mailed Nov. 16, 2010, from the Japan Patent Office in counterpart Japanese Patent Application No. 2005-232139, together with a partial English translation.

* cited by examiner

*Primary Examiner* — Lee S Cohen
(74) *Attorney, Agent, or Firm* — Scully, Scott, Murphy & Presser, P.C.

(57) ABSTRACT

A high-frequency treatment instrument is provided with an electrode for treatment for performing a high-frequency treatment at a treatment portion. The treatment portion protrudes from an insertion portion having an electrical insulation. The treatment portion protruding from the insertion portion is provided with the electrode for treatment provided with a plurality of electrode portions. The treatment performances of the plurality of electrode portions are different.

7 Claims, 9 Drawing Sheets

HIGH FREQUENCY TREATMENT INSTRUMENT

This application claims benefit of Japanese Application No. 2005-232139 filed in Japan on Aug. 10, 2005, the contents of which are incorporated by this reference.

BACKGROUND OF THE INVENTION

1. Field of the Invention

The present invention relates to a high-frequency treatment instrument inserted into a body cavity for incision or coagulation of a living tissue such as mucus membrane with a high-frequency electric current.

2. Description of the Related Art

Recently, surgeries using laparoscope are performed with the purpose of reducing invasion into a patient. In the surgery using laparoscope, a trocar for guiding an endoscope for observation into a body cavity and a trocar for guiding a treatment instrument to a portion to be treated are punctured into an abdominal portion of a patient without abdominal laparotomy, and a treatment procedure is performed while the treatment instrument and the portion to be treated are observed with the endoscope. In this type of surgery, a high-frequency power supply device and a high-frequency treatment device provided with a high-frequency treatment instrument are used. The high-frequency power supply device supplies a high-frequency electric current for treatment such as incision, coagulation and the like for the living tissue of the portion to be treated. The high-frequency treatment instrument is to give a treatment for the portion to be treated.

Also, with an endoscope having flexibility at an insertion portion to be inserted through an oral cavity, an anus or the like, the high-frequency treatment instrument is introduced into the body cavity through a treatment-instrument insertion channel provided to the endoscope for a treatment such as incision, coagulation and the like of the portion to be treated.

The high-frequency treatment instrument is provided with an electrode. When a treatment such as incision, coagulation or the like is to be performed with the high-frequency treatment instrument, the electrode is brought into contact with the living tissue such as mucous membrane and a high-frequency electric current is conducted to the electrode for treatment. When a treatment such as incision, coagulation is to be performed with the high-frequency treatment instrument, the electrode is protruded from a tip end of a sheath, which is the insertion portion having electric insulation. When a coagulation treatment is to be performed on a mucous membrane, an operator brings the electrode conducted with the high-frequency electric current into contact with the mucous membrane and keeps it. On the other hand, at incision or ablation, the operator brings the electrode conducted with the high-frequency electric current to the portion to be treated and moves the electrode in the direction of ablation.

In the high-frequency treatment devices, there are known a monopolar type and a bipolar type.

The monopolar type treatment instrument requires a return electrode in addition to the high-frequency treatment instrument provided with an electrode. The return electrode is brought into surface contact with the surface of the body other than the portion to be treated. The monopolar type treatment device is configured such that the high-frequency electric current outputted from the high-frequency cautery power supply device flows from an electrode provided at the high-frequency treatment instrument via the living tissue, which is the treatment target in contact with the electrode, and returns to the high-frequency cautery power supply device through the return electrode in surface contact with the body surface.

On the other hand, in the bipolar type treatment device, a high-frequency treatment instrument provided with an electrode for treatment and a return electrode is used. The bipolar type treatment device is configured such that the high-frequency electric current outputted from the high-frequency cautery power supply device flows from the electrode for treatment provided at the high-frequency treatment instrument via the living tissue, which is the treatment target in contact with the electrode for treatment, and returns to the high-frequency cautery power supply device through the return electrode. That is, the bipolar type treatment device does not need a return electrode to be brought into surface contact with the body surface.

Japanese Patent Laid-Open Publication No. 8-299355 discloses, for example, a high-frequency knife configured so that puncture into a deep tissue which should not be incised by mistake or unnecessary cautery is prevented during incision of a mucous membrane. This high-frequency knife aims to perform incision by providing an insulating tip larger than the knife at the tip end of the knife for electrode.

Therefore, if bleeding occurs during an incision treatment, it is necessary to replace this high-frequency knife by a high-frequency treatment instrument or the like with excellent coagulation performance and time and labor are required till hemostasis.

SUMMARY OF THE INVENTION

A high-frequency treatment instrument provided with an electrode for treatment for a high-frequency treatment at a treatment portion comprises an insertion portion having electrical insulation and an electrode for treatment provided with a plurality of electrodes provided at the treatment portion protruded from this insertion portion and exerting different treatment performances.

The above and other objects, features and advantages of the invention will become more clearly understood from the following description referring to the accompanying drawings.

BRIEF DESCRIPTION OF THE DRAWINGS

FIGS. 1 to 4 show a first embodiment of the present invention;

FIGS. 5 to 10 show a second embodiment of the present invention;

FIGS. 11 to 19 show a third embodiment of the present invention;

DESCRIPTION OF THE PREFERRED EMBODIMENTS

Embodiment of the present invention will be described below referring to the attached drawings.

A first embodiment of the present invention will be described referring to FIGS. 1 to 4.

Figure 1:
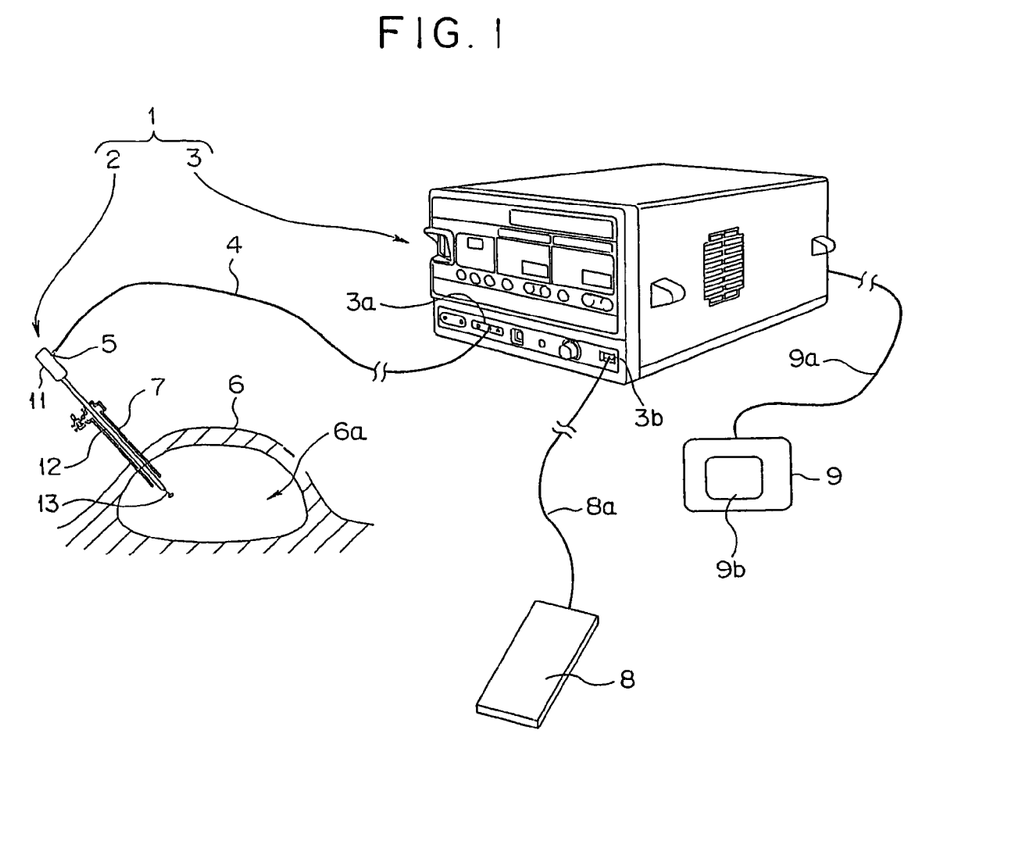
FIG. 1 is a view for explaining a configuration of a high-frequency treatment device.

As shown in FIG. 1, a high-frequency treatment device 1 comprises a high-frequency treatment instrument 2 and a high-frequency power supply 3. The illustrated high-frequency treatment instrument 2 performs coagulation and incision of a living tissue by flowing a high-frequency electric current to the living tissue. The high-frequency power supply 3 supplies the high-frequency electric current to the high-frequency treatment instrument 2. The high-frequency power supply 3 incorporates a high-frequency generation circuit for generating a high frequency, an HF output amplifier for electrically amplifying the high frequency and the like. Two output ends of the HF output amplifier are connected to an active electrode 3a and a patient electrode 3b, respectively.

The high-frequency treatment instrument 2 and the high-frequency power supply 3 are electrically connected to each other through an active cord 4. Specifically, one end of the active cord 4 is detachably connected to an electric connection portion 5 provided to the high-frequency treatment instrument 2. The other end of the active cord 4 is connected to an active electrode 3a, which is an active cord connection portion provided at the high-frequency power supply 3.

The high-frequency treatment instrument 2 is introduced into an abdominal cavity 6a, for example, through a trocar 7 punctured into an abdominal portion of a patient 6. On the back face side, for example, of the patient 6, a counter electrode plate 8 configured to be brought into contact in a wide area is arranged. From the counter electrode plate 8, a counter electrode plate cord 8a is extended. An end of the counter electrode plate cord 8a is connected to a patient electrode 3b, which is a counter electrode plate cord connection portion of the high-frequency power supply 3.

To the high-frequency power supply 3, a connection cord 9a extending from a foot switch 9 is connected. The foot switch 9 supplies a high-frequency electric current from the high-frequency power supply 3 to the high-frequency treatment instrument 2 by ON operation of a pedal portion 9b. On the other hand, the foot switch 9 stops supply of the high-frequency electric current by OFF operation of the pedal portion 9b. When the pedal portion 9b of the foot switch 9 is operated on by an operator, the high-frequency electric current flows through the active electrode 3a, the active cord 4, the electric connection portion 5, an electrode for treatment of the high-frequency treatment instrument 2, which will be described later, a living tissue and the counter electrode plate 8 and returns to the patient electrode 3b.

The high-frequency treatment instrument 2 comprises a gripping portion 11, an insertion portion 12 and a treatment portion 13. The insertion portion 12 protrudes from a tip-end face of the gripping portion 11 by a predetermined amount. The treatment portion 13 protrudes from a tip-end face of the insertion portion 12 by a predetermined amount. At a side portion, for example, of the gripping portion 11, the electric connection portion 5 is provided. The exterior of the gripping portion 11 and the insertion portion 12 is formed from a ceramic or resin member, for example, having insulation.

Figures 2, 3:
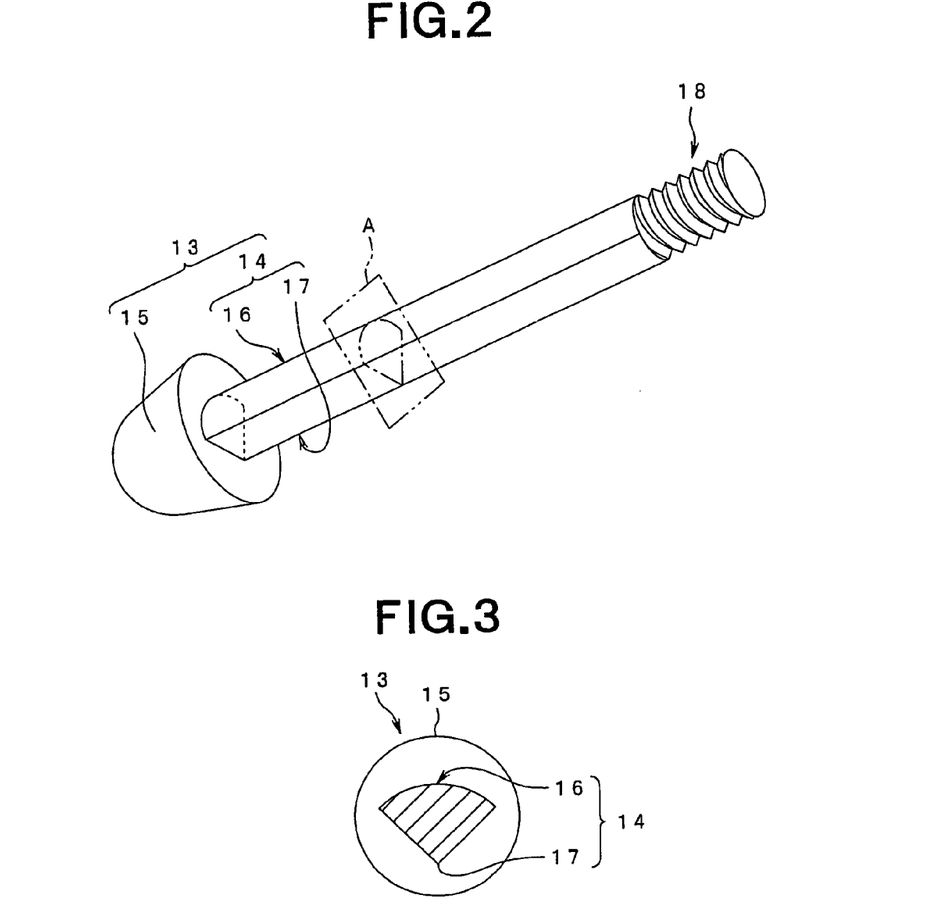
FIG. 2 is a view for explaining a treatment portion provided with an electrode for treatment constituting the high-frequency treatment instrument.
FIG. 3 is a view for explaining a sectional shape of the electrode for treatment and a sectional view of a state cut on the A surface in FIG. 2 and seen in the tip-end direction.

As shown in FIG. 2, the treatment portion 13 of this embodiment comprises a treatment electrode 14 and a contact portion 15. The contact portion 15 is formed of a heat resistance electrical insulating member such as a resin member or a ceramic, for example, and formed in the shape largely expanded from the outer dimension of the treatment electrode 14. A tip end portion of the contact portion 15 is formed in a curved shape, a semi-spherical shape, for example, considering its contact with a living tissue. The contact portion 15 is integrally provided at the tip end portion of the treatment electrode 14 by adhesion or integral molding, for example.

On the other hand, the treatment electrode 14 is formed of a metal member such as stainless, for example. The treatment electrode 14 is provided with two electrode portions 16, 17 exerting different treatment performances. As shown in FIG. 3, the sectional shape of the treatment electrode 14 is a fan shape. The first electrode portion 16 is an electrode portion for coagulation and its surface area is set large by being provided on the arc side of the fan shape. On the other hand, the second electrode portion 17 is an electrode portion for incision and is a sharp tip end on the center angle side of the fan shape. The fan shape is set as appropriate according to the purpose of use.

The treatment electrode 14 has a male thread portion 18 at its base end. The male thread portion 18 is configured to be screwed with a female thread portion provided at a conductive member, not shown, provided at the tip end portion of the insertion portion 12. That is, the treatment electrode 14 constituting the treatment portion 13 is integrally configured by screwing to the insertion portion 12.

Action of the high-frequency treatment instrument 2 provided with the above configured treatment portion 13 will be described.

First, a user prepares the active cord 4 and the counter electrode plate 8. The user connects one end of the active cord 4 to the active electrode 3a provided at the high-frequency power supply 3. Also, the user connects the other end of the active cord 4 to the electric connection portion 5 provided at the gripping portion 11. On the other hand, the user connects the counter electrode plate cord 8a provided at the counter electrode plate 8 to the patient electrode 3b of the high-frequency power supply 3. And the user arranges the counter electrode plate 8 at a predetermined position of the patient.

Next, the user introduces the treatment portion 13 and the insertion portion 12 of the high-frequency treatment instrument 2 through a trocar punctured into an abdominal cavity, not shown, for example, for treatment with the purpose of incision of a portion to be treated. And the user opposes the second electrode portion 17 provided at the treatment portion 13 to the portion to be treated while observing an endoscope image, for example, displayed on a screen of a display device, not shown. Here, the user performs ON-operation on the pedal portion 9b of the foot switch 9. Then, the high-frequency electric current is outputted from the high-frequency power supply 3. The high-frequency electric current is supplied to the treatment electrode 14 through the active electrode 3a, the active cord 4 and a conductive member. And by moving the second electrode portion 17 by the user in contact with the portion to be treated, the high-frequency electric current flows through the second electrode 17, the living tissue, the counter electrode plate 8 and the counter electrode plate cord 8a and returns to the patient electrode 3b. Then, the portion to be treated in contact with the second electrode portion 17 is incised with the movement of the second electrode portion 17.

If those concerned or the like confirm generation of bleeding on the screen during the incision by the second electrode portion 17, the user performs OFF-operation on the pedal portion 9b of the foot switch 9. After that, the user reverses the high-frequency treatment instrument 2 by 180 degrees so as to oppose the first electrode portion 16 instead of the second electrode portion 17 of the treatment portion 13 to the bleeding portion. Then, the user performs ON-operation on the pedal portion 9b of the foot switch 9. Then, the high-frequency electric current outputted from the high-frequency power supply 3 is supplied to the treatment electrode 14. Here, the user presses the first electrode portion 16 onto the vicinity of the bleeding portion, which is the portion to be treated. Then, the high-frequency electric current flows through the first electrode portion 16, the living tissue, the counter electrode plate 8, and the counter electrode plate cord 8a and returns to the patient electrode 3b, the portion touched by the first electrode portion 16 is coagulated and bleeding is stopped.

Since the contact portion 15 is provided at the tip end side of the treatment portion 13, during an incision treatment by the second electrode portion 17 and during a coagulation treatment by the first electrode portion 16, the tip end of the treatment electrode 14 is prevented from contacting the living tissue.

In this way, the electrode portion for incision and the electrode portion for coagulation with different treatment performances are provided at the treatment electrode constituting the treatment portion of the high-frequency treatment instrument. Therefore, by supplying the high-frequency electric current to the high-frequency treatment instrument and bringing the electrode portion for incision provided at the treatment portion into contact with the portion to be treated, the living tissue can be incised. On the other hand, by supplying the high-frequency electric current to the high-frequency treatment instrument and bringing the electrode portion for coagulation provided at the treatment portion into contact with the portion to be treated, the living tissue can be coagulated. That is, with the high-frequency treatment instrument of this embodiment, an incision treatment and a coagulation treatment can be carried out with a single high-frequency treatment instrument without insertion or withdrawal of the high-frequency treatment instrument introduced into the body cavity once, in other words, without replacing the high-frequency treatment instrument. Therefore, the operator can conduct a hemostatic treatment in a reduced time even if bleeding occurs in the incision treatment.

Figure 4:
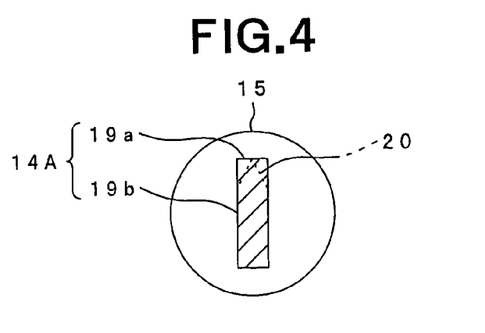
FIG. 4 is a sectional view for explaining another configuration of the electrode for treatment.

The sectional shape of the treatment electrode 14 provided with a plurality of treatment performances constituting the treatment portion 13 is not limited to the fan shape. For example, it may be configured in a rectangular shape as the sectional shape of a treatment electrode 14A as shown in FIG. 4. In this treatment electrode 14A, a short side portion 19a is an electrode portion for incision, while a long side portion 19b is an electrode portion for coagulation.

Also, in the treatment electrode 14A shown in FIG. 4, the short side portion 19a may be configured to have a sharp angle portion 20, which is sharp at the tip end, as shown by a broken line, for example. This sharp angle portion 20 is configured as an electrode portion for incision which cuts sharper than the short side portion 19a. That is, the treatment electrode 14A provided with the sharp angle portion 20 comprises two electrode portions for incision with two different cutting edges and a pair of electrode portions for coagulation.

When bleeding occurs during the incision treatment with the short side portion 19a, for example, of the treatment electrode 14A shown in FIG. 4, the treatment portion 13 of the high-frequency treatment instrument 2 is rotated by 90 degrees so that the long side portion 19b is opposed to the bleeding portion and then, it is pressed down. By this, the bleeding portion is coagulated and bleeding can be stopped.

A second embodiment of the present invention will be described referring to FIGS. 5 to 10.

Figure 5:
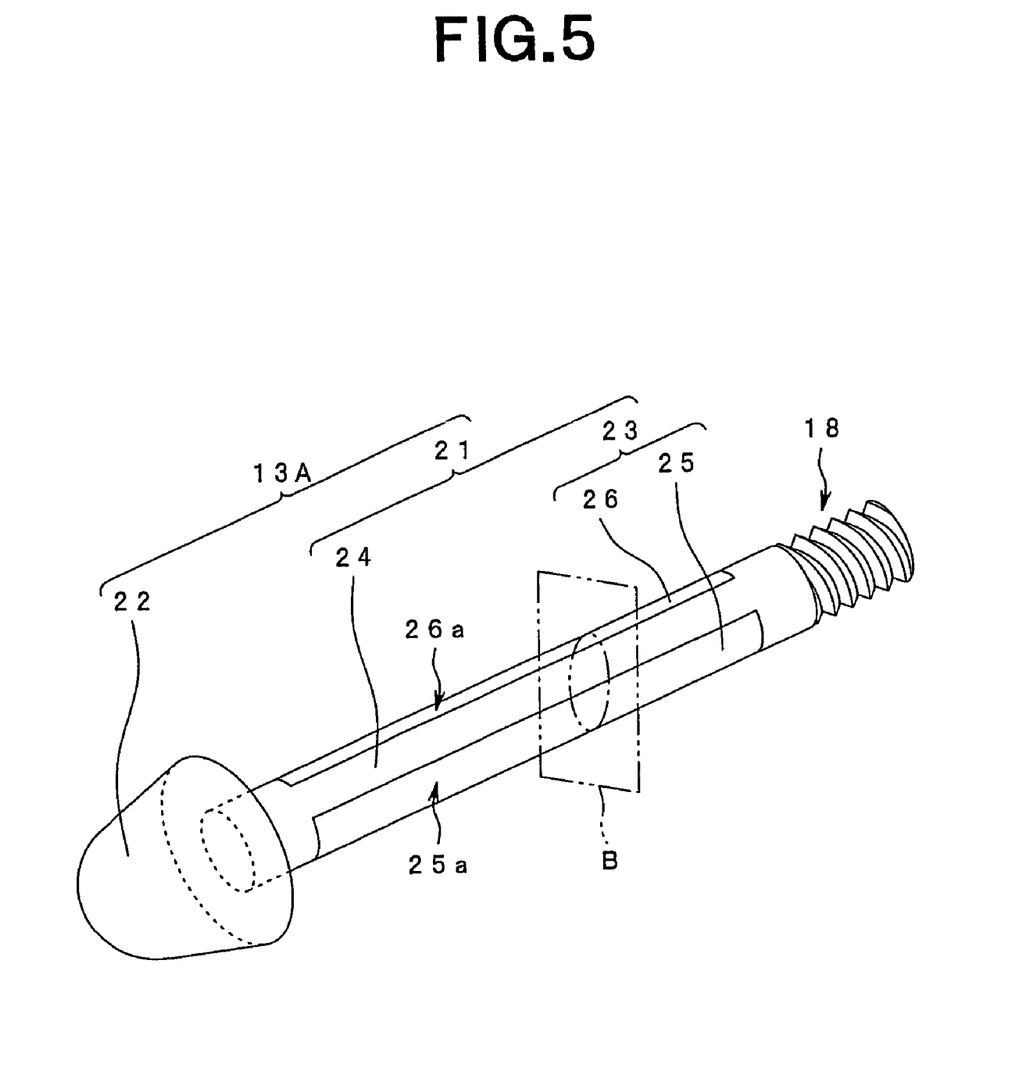
FIG. 5 is a view for explaining another configuration example of the treatment portion provided with the electrode for treatment constituting the high-frequency treatment instrument.

As shown in FIG. 5, a treatment portion 13A of the present embodiment comprises a columnar rod-state portion 21 and a contact portion 22, for example. The contact portion 22 is formed of a heat resistant electrical insulating member such as a resin member or a ceramic or the like as in the above first embodiment in the shape largely expanded from the outer dimension of the rod-state portion 21. A tip end portion of the contact portion 22 is formed in a curved shape, a semi-spherical shape, for example, considering its contact with a living tissue. The contact portion 22 is provided at the tip end portion of the rod-state portion 21 by integral molding, for example.

On the other hand, the rod-state portion 21 comprises a treatment electrode 23 and an insulation portion 24. The treatment electrode 23 comprises two electrode portions 25, 26, for example, exerting different treatment performances.

The insulation portion 24 is formed of an electrical insulating member constituting the contact portion 22, a resin member, for example. By providing the insulation portion 24, electrode surfaces 25a, 26a of the two electrode portions 25, 26 are divided having the insulating member between them with respect to the circumferential direction.

Figure 7:
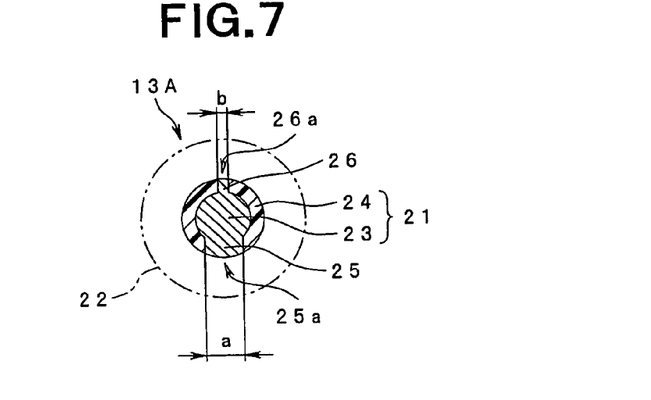
FIG. 7 is a view for explaining a relation between the electrode for treatment constituting the treatment portion and an electrical insulating member and B surface in FIG. 5 and a sectional view of C-C line in FIG. 6.

As shown in FIG. 7, the first electrode surface 25a of the first electrode portion 25 is an electrode portion for coagulation and its width dimension a on its exposed surface is set wider. On the other hand, the second electrode surface 26a of the second electrode portion 26 is an electrode portion for incision and its width dimension b on its exposed surface is set narrower than the width dimension a of the first electrode surface 25a.

Figure 6:
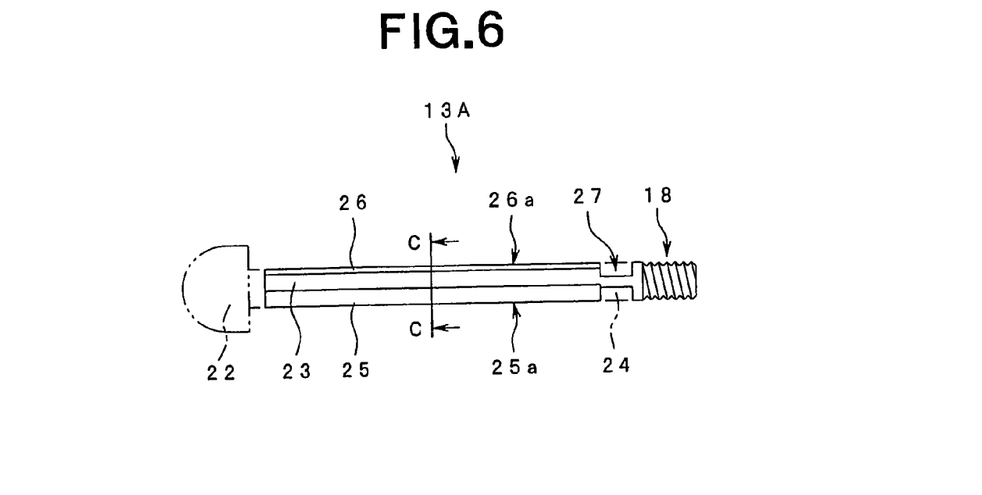
FIG. 6 is a view for explaining a relation between the electrode for treatment constituting the treatment portion and an electrical insulating member.

As shown in FIGS. 6 and 7, in the treatment portion 13A, an insulation portion 24 shown by a two-dot chain line or the like is integrally formed on the treatment electrode 23 shown by a solid line formed of a metal member such as stainless by integral molding. The treatment electrode 23 has the male thread portion 18 and a retaining groove 27 formed as well as the projection-shaped electrode portions 25, 26. The retaining groove 27 is a circumferential groove, for example, and provided in the circumferential state with a predetermined width dimension on the base end side of the treatment electrode 23. As shown in FIGS. 5 and 6, in the rod-state portion 21 in which the insulation portion 24 and the treatment electrode 23 are integrally configured, the insulation portion 24 is surely prevented from being removed from the treatment electrode 23. The length dimensions in the longitudinal direction of the electrode surfaces 25a, 26a are the same.

Action of the high-frequency treatment instrument 2 provided with the above configured treatment portion 13A will be described.

First, as described in the first embodiment, the user connects the active cord 4 and the counter electrode plate cord 8a provided at the counter electrode plate 8. Also, the user arranges the counter electrode plate 8 at a predetermined portion of a patient.

Next, the user introduces the treatment portion 13A and the insertion portion 12 of the high-frequency treatment instrument 2 into an abdominal cavity through a trocar, not shown, for a treatment with the purpose of incision of a portion to be treated. And the user opposes the second electrode surface 26a of the second electrode portion 26 provided at the treatment portion 13A to the portion to be treated while observing an endoscope image, for example, displayed on the screen of the display device, not shown. Here, the user performs ON-operation on the pedal portion 9b of the foot switch 9. Then, the high-frequency electric current is outputted from the high-frequency power supply 3. The high-frequency electric current is supplied to the treatment electrode 23 through the active electrode 3a, the active cord 4 and the conductive member. And when the user moves the second electrode surface 26a in contact with the portion to be treated, the high-frequency electric current flows through the second electrode surface 26a, the living tissue, the counter electrode plate 8 and the counter electrode plate cord 8a and returns to the patient electrode 3b. Then, the portion to be treated in contact with the second electrode surface 26a is incised with the movement of the second electrode surface 26a.

If those concerned confirm generation of bleeding on the screen during the incision by the second electrode surface 26a, the user performs OFF-operation on the pedal portion 9b of the foot switch 9. After that, the user reverses the treatment portion 13A of the high-frequency treatment instrument 2 by 180 degrees so as to oppose the first electrode surface 25a of the first electrode portion 25 instead of the second electrode surface 26a to the bleeding portion. Then, the user performs ON-operation on the pedal portion 9b of the foot switch 9. Then, the high-frequency electric current outputted from the high-frequency power supply 3 is supplied to the treatment electrode 23. Here, the user presses the first electrode surface 25a onto the vicinity of the bleeding portion, which is the portion to be treated. Then, the high-frequency electric current flows through the first electrode surface 25a, the living tissue, the counter electrode plate 8, and the counter electrode plate cord 8a and returns to the patient electrode 3b, the portion touched by the first electrode surface 25a is coagulated and bleeding is stopped.

In this way, to the treatment portion constituting the high-frequency treatment instrument, the first electrode surface for coagulation and the second electrode surface for incision divided by the insulation portion are provided. And by pressing and moving the second electrode surface on the portion to be treated, the incision treatment can be performed, while by keeping on pressing the first electrode surface on the portion to be treated for a predetermined time, the coagulation treatment can be performed. During this treatment, the contact area between the respective electrode surfaces and the portion to be treated can be maintained in a constant state all the time. Therefore, during the treatment, fluctuation of treatment performances caused by gradual or rapid change of the contact area between the electrode portion and the living tissue can be surely prevented. Thus, the operator can carry out the incision treatment, the coagulation treatment stably and smoothly without adjusting the contact state between the electrode surface and the portion to be treated by operation at hand.

The other actions and effects are the same as those of the above first embodiment.

Figure 8:
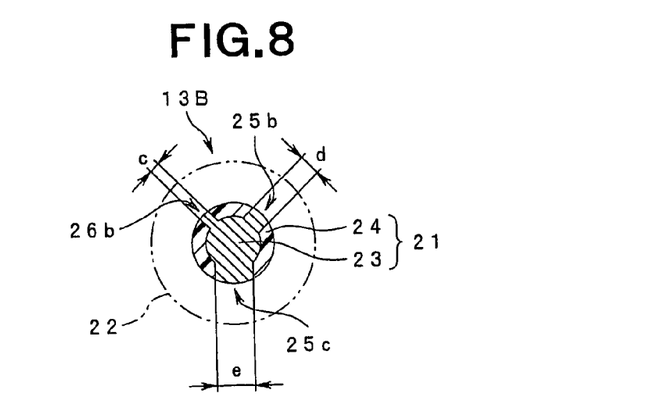
FIG. 8 is another configuration of the treatment portion and a view for explaining the relation between the electrode for treatment constituting the treatment portion and the electrical insulating member.

In the second embodiment, the configuration to provide the two electrode surfaces 25a, 26a at the treatment portion 13A is shown. However, the number of electrode surfaces is not limited to two. For example, a treatment portion 13B may be so configured with three electrode surfaces 26b, 25b, 25c divided in the circumferential direction, for example, as shown in FIG. 8.

In this configuration, by setting the width dimensions of the electrode surfaces 26b, 25b, 25c in the relation of c<d<e, the treatment portion 13A of the high-frequency treatment instrument is configured by one electrode portion for incision and two electrode portions for coagulation with different coagulation performances.

Also, in the second embodiment, the length dimension in the longitudinal direction is set to the same while the width dimension is varied so that the treatment performances of the electrode surfaces 25a, 26a provided on the treatment portion 13A are different. That is, the width dimension a and the width dimension b are set at different dimensions to obtain different treatment performances.

Figure 9:
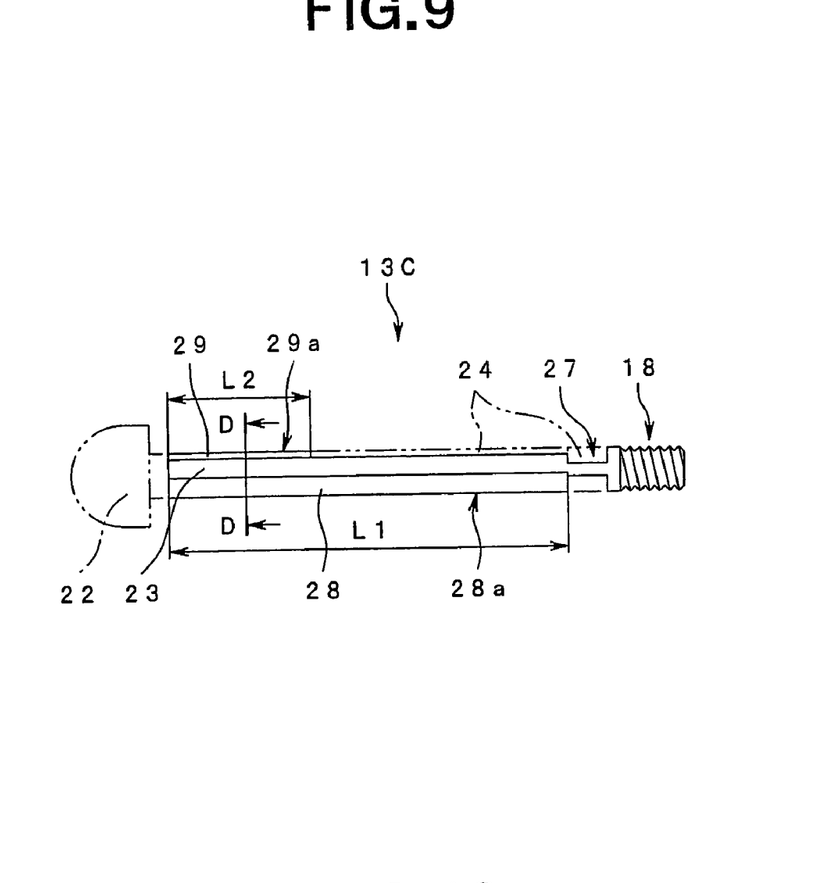
FIG. 9 is still another configuration of the treatment portion and a view for explaining the relation between the electrode for treatment constituting the treatment portion and the electrical insulating member.
Figure 10:
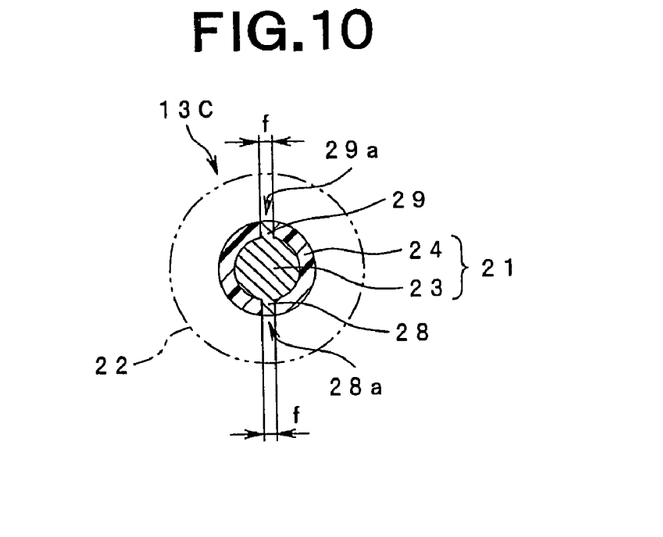
FIG. 10 is a sectional view of D-D line in FIG. 9.

On the other hand, in a treatment portion 13C shown in FIGS. 9 and 10, as shown in FIG. 10, the width dimension of an electrode surface 28a and the width dimension of an electrode surface 29a are set to the same dimension f. And as shown in FIG. 9, a relation of L1>L2 is established between a dimension L1 of the first electrode portion 28 in the longitudinal direction and a dimension L2 of the second electrode portion 29 in the longitudinal direction.

The treatment portion 13C can obtain two different treatment performances: an electrode surface for coagulation constituted by the first electrode surface 28a with the L1 dimension and an electrode surface for incision constituted by the second electrode surface 29a with the L2 dimension. With this treatment portion 13C, substantially the same action and effects can be obtained as those of the second embodiment.

In the above-mentioned embodiment, the treatment portion of the high-frequency treatment instrument is a monopolar type. The configuration of the treatment portion of a bipolar type will be described in an embodiment shown below.

A third embodiment of the present invention will be described referring to FIGS. 11 to 19.

Figure 11:
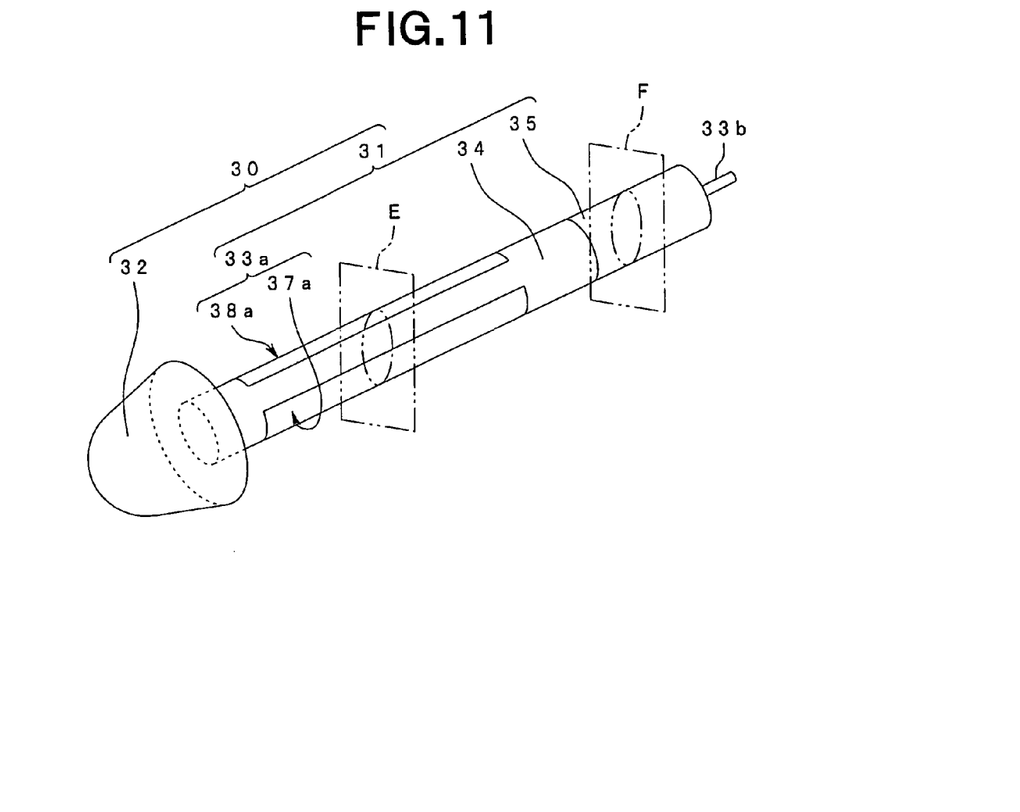
FIG. 11 is a view for explaining a configuration of the treatment portion provided with the electrode for treatment and an electrode for return.
Figure 12:
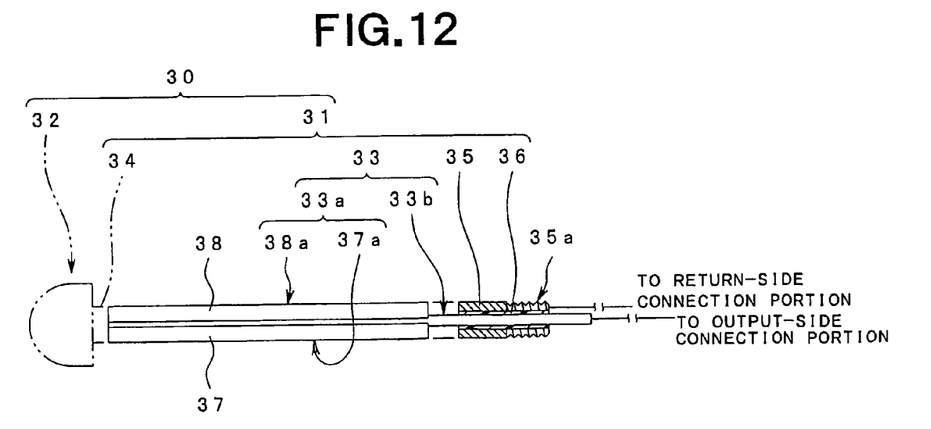
FIG. 12 is a view for explaining a relation between the electrode for treatment constituting the treatment portion and the electrical insulating member and the relation between the electrode for return and the electrical insulating member.

A treatment portion 30 of the present embodiment comprises, as shown in FIGS. 11 and 12, a columnar rod-state portion 31 and a contact portion 32. The contact portion 32 is, as with the above-mentioned embodiment, formed of a heat resistance electrical insulating member such as a resin member or a ceramic and formed in the shape largely expanded from the outer diameter dimension of the rod-state portion 31. A tip end portion of the contact portion 32 is formed in a curved shape, a semi-spherical shape, for example, considering its contact with a living tissue. The contact portion 32 is provided at the tip end portion of the rod-state portion 31 by integral molding, for example.

On the other hand, the rod-state portion 31 comprises a treatment electrode 33, a first insulation portion 34, a return electrode 35 and a second insulation portion 36. The treatment electrode 33 is provided with a large-diameter portion 33a and a small-diameter portion 33b. The large-diameter portion 33a is provided with two electrode portions 37, 38, for example, exerting different treatment performances. The first insulation portion 34 is integrally configured by the resin member constituting the contact portion 32. By providing the first insulation portion 34, electrode surfaces 37a, 38a of the two electrode portions 37, 38 are divided with an insulating member between them in the circumferential direction.

When the first insulation portion 34 and the treatment electrode 33 are to be configured integrally, the first insulation portion 34 is provided so as to cover and enclose the small-diameter portion 33b. The outer diameter dimension of the first insulation portion 34 covering the small-diameter portion 33b is set to the same diameter as the outer diameter dimension of the rod-state portion 31. The small-diameter portion 33b is protruded from the base end face of the first insulation portion 34 by a predetermined amount. Since the first insulation portion 34 is disposed to hold the large-diameter portion 33a, removal of the first insulation portion 34 from the treatment electrode 33 is surely prevented. The dimensions of the electrode surfaces 37a, 38a in the longitudinal direction are the same.

Figure 13:
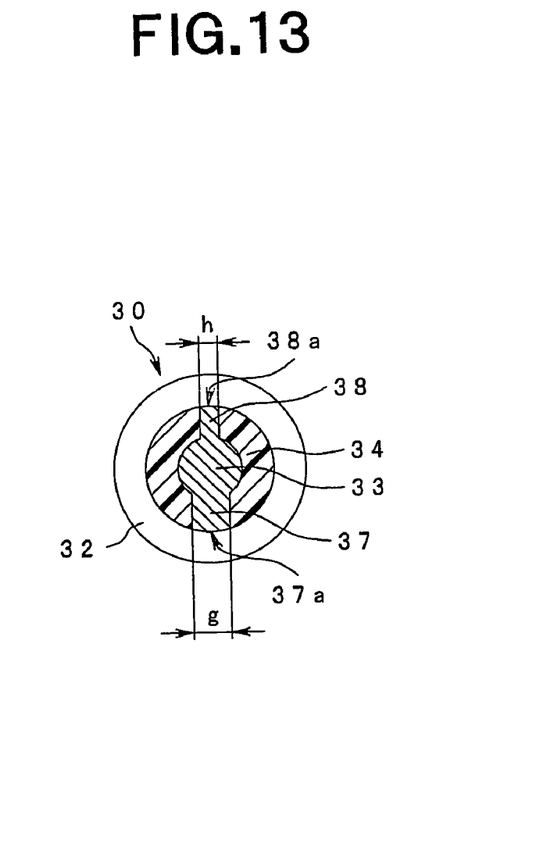
FIG. 13 is a view for explaining the relation between the electrode for treatment constituting the treatment portion and the electrical insulating member and a sectional view cut on E surface in FIG. 11 and seen in the tip-end direction.

As shown in FIG. 13, the first electrode surface 37a of the first electrode portion 37 is an electrode portion for coagulation, and a width dimension g of the exposed surface is set wider. On the other hand, the second electrode surface 38a of the second electrode portion 38 is an electrode portion for incision, and a width dimension h of the exposed surface is set smaller than the width dimension g of the first electrode surface 37a.

Figure 14:
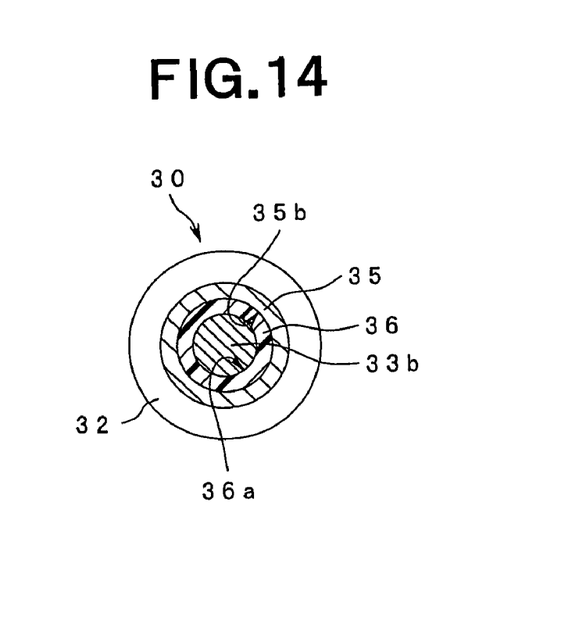
FIG. 14 is a view for explaining the relation between the electrode for return constituting the treatment portion and the electrical insulating member and a sectional view cut on F surface in FIG. 11 and seen in the tip-end direction.

On the other hand, the return electrode 35 is configured in the ring state as shown in FIGS. 12 and 14. A male thread portion 35a is provided at the base end side on the outer circumferential surface of the return electrode 35. In an inner hole 35b, which is a central through hole of the return electrode 35, a ring-state second insulation portion 36 is integrally provided. The second insulation portion 36 is provided with the inner hole 36a, which is the central through hole, through which the small-diameter portion 33b of the treatment electrode 33 is inserted and disposed. The return electrode 35 and the second insulation portion 36 are integrally molded or integrally configured by adhesion.

Here, a forming process of the treatment portion 30 is explained.

First, the treatment electrode 33 on which the first insulation portion 34 is integrally provided and the return electrode 35 on which the second insulation portion 36 is integrally provided are prepared. Next, the small-diameter portion 33b of the treatment electrode 33 is inserted into the inner hole 36a of the second insulation portion 36 integrally provided at the return electrode 35. And the end faces of the return electrode 35 and the second insulation portion 36 are brought into contact with the end face of the first insulation portion 34 provided at the base end portion of the large-diameter portion 33a constituting the treatment electrode 33. After that, the return electrode 35, the second insulation portion 36 and the first insulation portion 34 are integrally fixed by adhesion, for example, to constitute the treatment portion 30 shown in FIG. 11. In the treatment portion 3, the treatment electrode 33 and the return electrode 35 are surely prevented from electric contact with each other by the first insulation portion 34 and the second insulation portion 36. Also, the small-diameter portion 33b of the treatment electrode 33 is protruded by a predetermined amount from the base end faces of the return electrode 35 and the second insulation portion 36.

By connecting the treatment portion 30 to the insertion portion (not shown) of the high-frequency treatment instrument, not shown, the treatment electrode 33 and a base portion for active cord, not shown, are electrically connected to each other through a first conductive member provided in the insertion portion. Also, the return electrode 35 and a base portion for return cord, not shown, are electrically connected to each other through a second conductive member provided at the insertion portion.

Action of the high-frequency treatment instrument provided with the above configured treatment portion 30 will be described.

First, the user connects the active cord (not shown) and the return cord (not shown) to the respective base portions provided at the gripping portion of the high-frequency treatment instrument and the respective connection portion provided at the high-frequency power supply.

Next, the user introduces the treatment portion 30 and the insertion portion of the high-frequency treatment instrument into an abdominal cavity through a trocar, not shown, for a treatment with the purpose of incision of a portion to be treated. And the user opposes the second electrode surface 38a of the second electrode portion 38 provided at the treatment portion 30 to the portion to be treated while observing an endoscope image, for example, displayed on the screen of the display device, not shown. Here, the user performs ON-operation on the pedal portion 9b of the foot switch 9. Then, the high-frequency electric current is outputted from the high-frequency power supply 3. The high-frequency electric current is supplied to the active cord 4, the first conductive member, not shown, and the treatment electrode 33. And when the user moves the second electrode surface 38a in contact with the portion to be treated, the high-frequency electric current flows through the second electrode surface 38a, the portion to be treated, the return electrode 35, the second conductive member and the return cord and returns to the high-frequency power supply. Then, the portion in contact with the second electrode surface 38a is incised with the movement of the second electrode surface 38a.

If those concerned or the like confirm generation of bleeding on the screen during the incision by the second electrode surface 38a, the user performs OFF-operation on the pedal portion 9b of the foot switch 9. After that, the user reverses the treatment portion 30 of the high-frequency treatment instrument by 180 degrees so as to oppose the first electrode surface 37a of the first electrode portion 37 instead of the second electrode surface 38a to the bleeding portion. Then, the user performs ON-operation on the pedal portion 9b of the foot switch 9. Then, the high-frequency electric current outputted from the high-frequency power supply 3 is supplied to the treatment electrode 33 as mentioned above. Here, the user presses the first electrode surface 37a onto the vicinity of the bleeding portion, which is the portion to be treated. Then, the high-frequency electric current flows through the first electrode surface 37a, the portion to be treated, the return electrode 35, the second conductive member, and the return cord and returns to the high-frequency power supply, and the portion touched by the first electrode surface 37a is coagulated and bleeding is stopped.

In this way, the treatment electrode and the return electrode are provided at the treatment portion constituting the high-frequency treatment instrument so as to constitute the treatment portion as the bipolar type. And the electrode portion for incision and the electrode portion for coagulation with different treatment performances are provided at the treatment electrode. By pressing and moving the electrode portion for incision provided at the treatment electrode on the portion to be treated while supplying the high-frequency electric current, the incision treatment of the living tissue can be performed. On the other hand, by pressing the electrode portion for coagulation on the portion to be treated while the high-frequency electric current is supplied, coagulation of the living tissue can be performed.

That is, also in the bipolar type in the same way as the monopolar type, an incision treatment and a coagulation treatment can be carried out by one high-frequency treatment instrument introduced into a body cavity without replacing the treatment instrument. The other actions and effects are the same as those in the above-mentioned embodiments.

In the third embodiment, the dimensions in the longitudinal direction are set to the same dimension while the width dimension is changed so that treatment performances of the electrode surfaces 37a, 38a provided at the treatment portion 30 can be different. That is, the width dimension g and the width dimension h are set to different dimensions to obtain different treatment performances.

Figure 15:
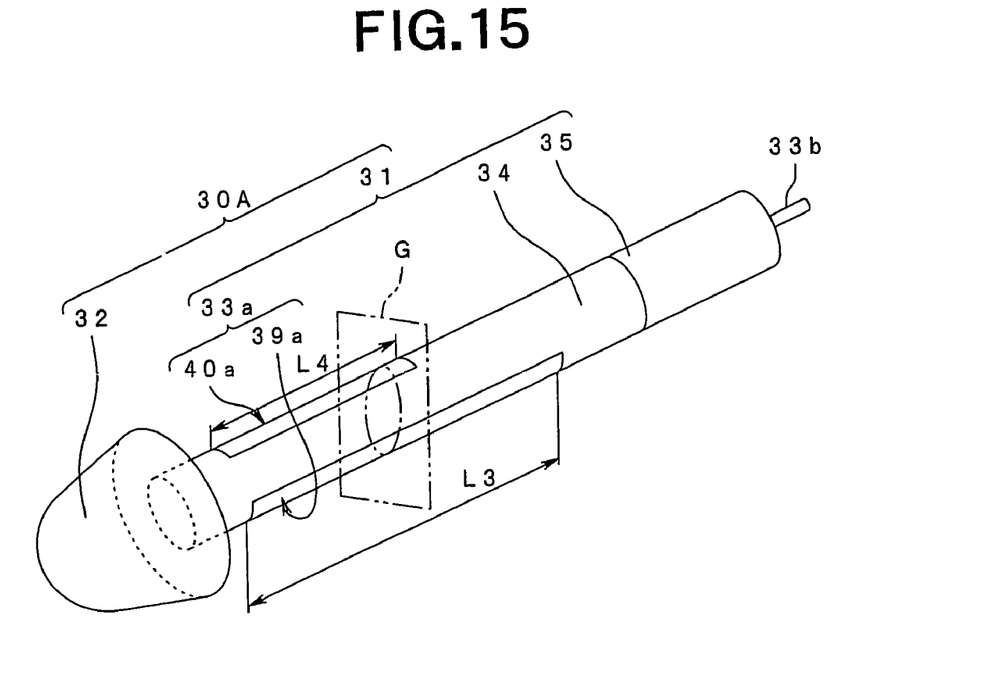
FIG. 15 is another configuration of the treatment portion provided with the electrode for treatment and the electrode for return and a view for explaining the relation among the electrode for treatment having an electrode surface with different dimension in the longitudinal direction, the electrode for return and the electrical insulating member.
Figure 16:
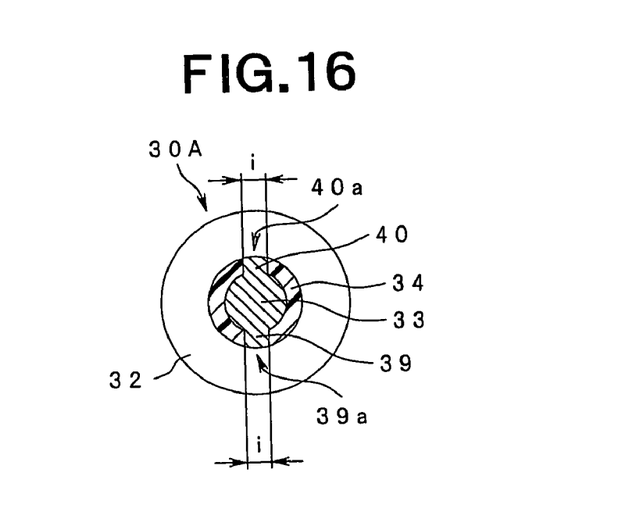
FIG. 16 is a sectional view cut on G surface in FIG. 15 and seen in the tip-end direction.

On the other hand, in a treatment portion 30A shown in FIGS. 15 and 16, the width dimension of an electrode surface 39a and the width dimension of an electrode surface 40a are set to the same dimension i, as shown in FIG. 16. And as shown in FIG. 15, a relation of L3>L4 is established between a dimension L3 of the first electrode portion 39 in the longitudinal direction and a dimension L4 of the second electrode portion 40 in the longitudinal direction.

The treatment portion 30A can obtain two different treatment performances: an electrode surface for coagulation constituted by the first electrode surface 39a with the L3 dimension and an electrode surface for incision constituted by the second electrode surface 40a with the L4 dimension. In this treatment portion 30A, substantially the same actions and effects can be obtained as those of the third embodiment.

Also, in the third embodiment, the treatment portion 30 is configured by dividing and providing the first electrode surface 37a and the second electrode surface 38a with the insulating member between them in the circumferential direction. However, the first electrode portion and the second electrode portion may be divided in the longitudinal direction with the insulating member between them. The configuration examples will be described referring to FIGS. 17 to 19.

Figure 17:
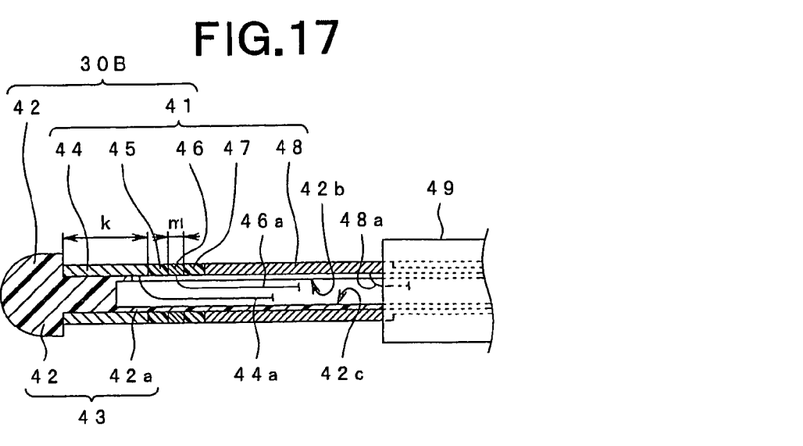
FIG. 17 is a view for explaining the configuration of the treatment portion provided with the electrode for treatment and the electrode for return, a first electrode portion and a second electrode portion being provided separately in the longitudinal direction at the electrode for treatment.

A treatment portion 30B shown in FIG. 17 comprises a tubular rod-state portion 41 and a contact portion 42. The contact portion 42 is constituted as a contact member 43. The contact member 43 is provided with a contact portion 42 and a tube portion 42a. The contact portion 42 is, in the same way as with the above-mentioned embodiments, formed of a heat resistant electrical insulating member such as a resin member or ceramic, and a slit 42b into which an electric wire which will be described later is inserted, is provided at the tube portion 42a. The contact portion 42 is formed in the shape largely expanded from the outer diameter dimension of the rod-state portion 41. A tip end portion of the contact portion 42 is formed in a curved shape, a semi-spherical shape, for example, considering its contact with a living tissue.

On the other hand, the rod-state portion 41 comprises a first treatment electrode 44, a first insulating member 45, a second treatment electrode 46, a second insulating member 47, and a return electrode 48 from the tip end side in this order. The treatment electrodes 44, 46, the return electrode 48 and the insulating members 45, 47 are configured in the ring state, respectively. The treatment electrodes 44, 46, the return electrode 48, and the insulating members 45, 47 are externally fitted and arranged on the tube portion 42a of the contact member 43 and integrally fixed by adhesion or the like. The first treatment electrode 44 is an electrode portion for coagulation and its length dimension k in the longitudinal direction is set longer. On the other hand, the second treatment electrode 46 is an electrode portion for incision and its length dimension m is set shorter than the length dimension k of the first treatment electrode 44.

An electric wire 44a extends from a predetermined position on the inner circumferential face side of the treatment electrode 44. An electric wire 46a extends from a predetermined position on the inner circumferential face side of the treatment electrode 46. An electric wire 48a extends from a predetermined position on the inner circumferential face side of the return electrode 48. These electric wires 44a, 46a, 48a are guided into an inner hole 42c of the tube portion 42 through a longitudinally elongated slit 42b. The base end portion of the electric wire 44a is electrically connected to a base portion for an active cord, not shown. The base end portion of the electric wire 46a is electrically connected to a base portion for an active cord, not shown. The base end portion of the electric wire 48a is electrically connected to a base portion for a return cord, not shown. Reference numeral 49 denotes an insertion portion.

Action of the high-frequency treatment instrument provided with the above-configured treatment portion 30B will be described.

First, the user connects the active cord (not shown) and the return cord (not shown) to the respective base portions provided at the gripping portion of the high-frequency treatment instrument and the respective connection portion provided at the high-frequency power supply.

Next, the user introduces the treatment portion 30B and the insertion portion 49 of the high-frequency treatment instrument into an abdominal cavity through a trocar, not shown, for a treatment with the purpose of incision of a portion to be treated. And the user opposes the surface of the second treatment electrode 46 provided at the treatment portion 30B to the portion to be treated while observing an endoscope image, for example, displayed on the screen of the display device, not shown. Here, the user performs ON-operation on the pedal for incision of the foot switch 9. Then, the high-frequency electric current is outputted from the high-frequency power supply 3. The high-frequency electric current is supplied to the second treatment electrode 46 through the active cord and the electric wire 46a. And when the user moves the second treatment electrode 46 in contact with the portion to be treated, the high-frequency electric current flows through the second treatment electrode 46, the portion to be treated, the return electrode 48, the electric wire 48a and the return cord and returns to the high-frequency power supply. Then, the portion in contact with the surface of the second treatment electrode 46 is incised with the movement of the surface of the second treatment electrode 46.

If those concerned or the like confirm generation of bleeding on the screen during the incision by the second treatment electrode 46, the user performs OFF-operation on the pedal for incision of the foot switch 9. After that, the user moves the high-frequency treatment instrument to the hand side and opposes the surface of the first treatment electrode 44 instead of the second treatment electrode 46 to the bleeding portion. Then, the user performs ON-operation on the pedal for coagulation of the foot switch 9. Then, the high-frequency electric current outputted from the high-frequency power supply 3 is supplied to the first treatment electrode 44 through the active cord and the electric wire 44a. Here, the user presses the surface of the first treatment electrode 44 onto the vicinity of the bleeding portion, which is the portion to be treated. Then, the high-frequency electric current flows through the first treatment electrode 44, the portion to be treated, the return electrode 48, the electric wire 48a, and the return cord and returns to the high-frequency power supply, and the portion touched by the surface of the first treatment electrode 44 is coagulated and bleeding is stopped.

In this way, by dividing and providing an electrode portion for coagulation and an electrode portion for incision separately in the longitudinal direction, different treatments can be carried out smoothly by moving the high-frequency treatment instrument back and forth without rotating it. The other actions and effects are the same as those of the above-mentioned embodiments.

Electrode surfaces may be provided on the ring-state treatment electrodes 44, 46 so that a contact area between the electrode surface and the portion to be treated is constant all the time during the treatment.

Figure 18:
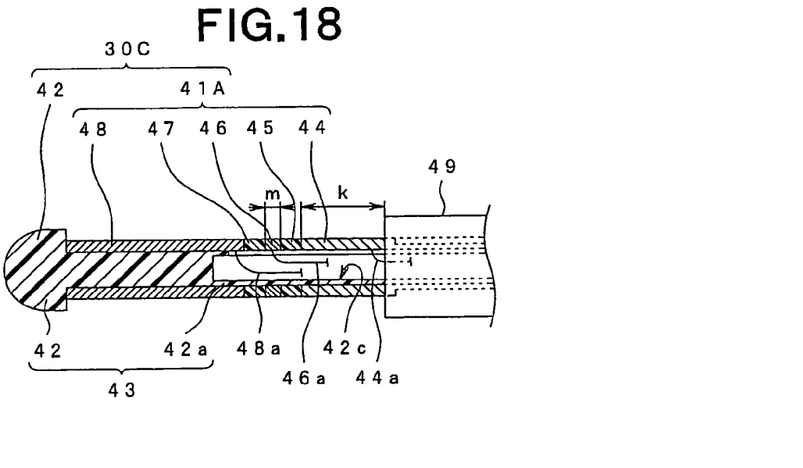
FIG. 18 is a view for explaining another configuration of the treatment portion provided with the electrode for treatment and the electrode for return, a first electrode portion and a second electrode portion being provided separately in the longitudinal direction at the electrode for treatment.

In the present embodiment, the rod-state portion 41 of the treatment portion 30B is constituted by arranging the first treatment electrode 44, the first insulating member 45, the second treatment electrode 46, the second insulating member 47 and the return electrode 48 from the tip end side in this order. However, as shown in FIG. 18, for example, a rod-state portion 41A of a treatment portion 30C may be constituted by arranging the first treatment electrode 44, the first insulating member 45, the second treatment electrode 46, the second insulating member 47 and the return electrode 48 from the sheath side in this order. Moreover, in the bipolar-type high-frequency treatment instrument, the electrode portions may be divided and provided in the circumferential direction.

Figure 19:
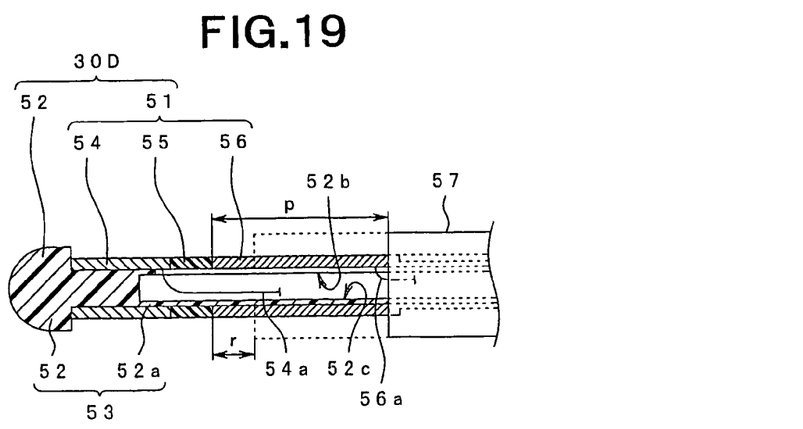
FIG. 19 is a view for explaining the treatment portion provided with the electrode for treatment and the electrode for return in the configuration to change treatment performance of the electrode for treatment by moving a sheath forward/backward.

A treatment portion 30D comprises, as shown in FIG. 19, a tubular rod-state portion 51 and a contact portion 52. The contact portion 52 is constituted as a contact member 53. The contact member 53 is, in the same way as the above-mentioned embodiments, formed of a heat resistant electrical insulating member such as a resin member or ceramic, and a slit 52b into which an electric wire is inserted, which will be described later, is provided at the tube portion 52a. The contact portion 52 is formed in the shape largely expanded from the outer diameter dimension of the rod-state portion 51. A tip end portion of the contact portion 52 is formed in a curved shape, a semi-spherical shape, for example, considering its contact with a living tissue.

On the other hand, the rod-state portion 51 comprises a return electrode 54, an insulating member 55, and a treatment electrode 56 from the tip end side in this order. The treatment electrode 56, the return electrode 54 and the insulating member 55 are configured in the ring state, respectively. The treatment electrode 56, the return electrode 54 and the insulating member 55 are externally fitted and arranged on the tube portion 52a of the contact member 53 and integrally fixed by adhesion or the like. And they are arranged on the outer circumference side of a sheath 57 constituting an insertion porton, and the treatment electrode 56, and the shealth 57 is configured Capable of moving forward/backward with respect to the treatment electrode 56. When a sheath 57 is arranged on the base end side as shown by a solid line in the figure, the treatment electrode 56 becomes an electrode portion for coagulation. On the other hand, when the sheath 57 is moved to the tip end side as shown by a broken line in the figure, the treatment electrode 56 becomes an electrode portion for incision. That is, the treatment electrode 56 constitutes an electrode portion for coagulation when the length dimension is set long as a dimension p, while it constitutes an electrode portion for incision when the dimension is set short as a dimension r.

An electric wire 56a extends from a predetermined position of an inner circumferential face of the treatment electrode 56. An electric wire 54a extends from a predetermined position of an inner circumferential face of the return electrode 54. These electric wires 56a, 54a are guided into an inner hole 52c of the tube portion 52a through a longitudinally elongated slit 52b. The base end portion of the electric wire 56a is electrically connected to a base portion for active cord, not shown, while the base end portion of the electric wire 54a is electrically connected to a base portion for return cord, not shown.

Action of the high-frequency treatment instrument provided with the above-configured treatment portion 30D will be described.

First, the user connects the active cord (not shown) and the return cord (not shown) to the respective base portions provided at the gripping portion of the high-frequency treatment instrument and the respective connection portion provided at the high-frequency power supply.

Next, the user sets the sheath 57 of the high-frequency treatment instrument at a position shown by a broken line for a treatment with the purpose of incision of a portion to be treated. After that, the user introduces the treatment portion 30D of the high-frequency treatment instrument and the shealth 57 into an abdominal cavity through a trocar, not shown. And the user opposes the surface of the treatment electrode 56 constituted at the treatment portion 30D to the portion to be treated while observing an endoscope image, for example, displayed on the screen of the display device, not shown. Here, the user performs ON-operation on the pedal portion 9b of the foot switch 9. Then, the high-frequency electric current is outputted from the high-frequency power supply 3. The high-frequency electric current is supplied to the treatment electrode 56 through the active cord and the electric wire 56a. And when the user moves the treatment electrode 56 in contact with the portion to be treated, the high-frequency electric current flows through the treatment electrode 56, the portion to be treated, the return electrode 54, the electric wire 54a and the return cord and returns to the high-frequency power supply. Then, the portion in contact with the surface of the treatment electrode 56 is incised with the movement of the surface of the treatment electrode 56.

If those concerned or the like confirm generation of bleeding on the screen during the incision by the treatment electrode 56, the user performs OFF-operation on the pedal portion 9b of the foot switch 9. After that, the user moves the sheath 57 of the high-frequency treatment instrument from the position shown by the broken line to a position shown by a solid line, for example, to oppose the electrode portion for coagulation instead of the electrode portion for incision to the bleeding portion. Then, the treatment electrode 56 constituted as an electrode portion for incision provided at the treatment portion 30D is constituted as an electrode portion for coagulation. The surface of the treatment electrode 56 opposes the bleeding portion. And the user performs ON-operation on the pedal portion 9b of the foot switch 9. Then, the high-frequency electric current outputted from the high-frequency power supply 3 is supplied to the treatment electrode 56. Here, the user presses the surface of the treatment electrode 56 onto the vicinity of the bleeding portion, which is the portion to be treated. Then, the high-frequency electric current flows through the treatment electrode 56, the portion to be treated, the return electrode 54, the electric wire 54a, and the return cord and returns to the high-frequency power supply, and the portion touched by the surface of the treatment electrode 56 constituted as the electrode portion for coagulation is coagulated and bleeding is stopped.

In this way, the return electrode, the insulating member and the treatment electrode are arranged in the longitudinal direction of the treatment portion from the tip end side in this order and the insertion portion is constituted capable of moving forward/backward with respect to the treatment electrode. In this configuration, by moving the insertion portion forward/backward, the length dimension of the treatment electrode protruded from the tip end face of the insertion portion is adjusted as appropriate. By setting the length dimension of the treatment electrode protruding from the tip end face of the insertion portion as appropriate, the high-frequency treatment instrument capable of freely changing the treatment performance of the treatment portion can be constituted.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A monopolar type high frequency treatment instrument for performing a high frequency treatment of a living tissue, the monopolar type high frequency treatment instrument comprising:
    an insertion portion comprising an electrical insulating member formed on the exterior of the insertion portion; and
    a treatment portion provided in connection with the insertion portion and provided with a treatment electrode including an incision electrode portion configured to perform an incision treatment of the living tissue and a coagulation electrode portion configured to perform a coagulation treatment of the living tissue, the monopolar type high frequency treatment electrode including on an outer circumferential surface side thereof an electrical insulating member, the incision electrode portion and the coagulation electrode portion having electrode surfaces which are exposed by the electrical insulating member,
    wherein the treatment electrode is configured to flow current through the living tissue from the electrode surface of one electrode portion which is one of the incision electrode portion and the coagulation electrode portion and which contacts a living tissue as a portion to be treated to a counter electrode plate which is a separate body from the treatment electrode and which is brought into surface contact with a body surface other than the portion to be treated.

2. The monopolar type high frequency treatment instrument according to claim 1, wherein the electrical insulating member of the treatment portion is arranged between the incision electrode portion and the coagulation electrode portion, and divides the electrode surface of the incision electrode portion and the electrode surface of the coagulation electrode portion.

3. The monopolar type high frequency treatment instrument according to claim 2, wherein the electrode surface of the incision electrode portion and the electrode surface of the coagulation electrode portion are exposed in the longitudinal direction of the treatment portion by the electrical insulating member of the treatment portion, and the exposed electrode surfaces are arranged in the divided manner in the circumferential direction of the treatment portion.

4. The monopolar type high frequency treatment instrument according to claim 3, wherein:
    the electrode surface of the incision electrode portion and the electrode surface of the coagulation electrode portion provided to the treatment electrode have the same length dimension in the longitudinal direction and have different width dimensions, and
    the width of the electrode surface of the incision electrode portion is smaller than the width of the electrode surface of the coagulation electrode portion.

5. The monopolar type high frequency treatment instrument according to claim 3, wherein:
    the electrode surface of the incision electrode portion and the electrode surface of the coagulation electrode portion provided to the treatment electrode have the same width dimension and have different length dimensions in the longitudinal direction, and
    the length of the electrode surface of the incision electrode portion is smaller than the length of the electrode surface of the coagulation electrode portion.

6. The monopolar type high frequency treatment instrument according to claim 1, wherein the treatment electrode is provided with a male thread portion at a base end thereof, which is screwed with a female thread portion provided at a tip-end portion of the insertion portion.

7. The monopolar type high frequency treatment instrument according to claim 1, wherein the electrode surface of the incision electrode portion and the electrode surface of the coagulation electrode portion are provided at positions substantially opposed to each other on the outer circumferential surface of the treatment electrode.

* * * * *